(12) United States Patent
Oakley et al.

(10) Patent No.: US 10,195,357 B2
(45) Date of Patent: Feb. 5, 2019

(54) DRUG DELIVERY DEVICE

(71) Applicant: Sanofi, Paris (FR)

(72) Inventors: Tom Oakley, Cambridge (GB); Karl Hewson, Cambridge (GB); Stuart Milne, Buckden St. Neots (GB); Mark Pawulski, Buckingham (GB)

(73) Assignee: Sanofi, Paris (FR)

( * ) Notice: Subject to any disclaimer, the term of this patent is extended or adjusted under 35 U.S.C. 154(b) by 332 days.

(21) Appl. No.: 14/905,390

(22) PCT Filed: Jul. 17, 2014

(86) PCT No.: PCT/EP2014/065341
§ 371 (c)(1),
(2) Date: Jan. 15, 2016

(87) PCT Pub. No.: WO2015/007822
PCT Pub. Date: Jan. 22, 2015

(65) Prior Publication Data
US 2016/0151572 A1    Jun. 2, 2016

(30) Foreign Application Priority Data

Jul. 17, 2013 (EP) ..................................... 13176886

(51) Int. Cl.
*A61M 5/315* (2006.01)
*A61M 5/24* (2006.01)
*A61M 5/31* (2006.01)

(52) U.S. Cl.
CPC ...... *A61M 5/3155* (2013.01); *A61M 5/31528* (2013.01); *A61M 5/31541* (2013.01);
(Continued)

(58) Field of Classification Search
CPC ............ A61M 5/3155; A61M 5/31528; A61M 5/31541; A61M 5/31548; A61M 5/31553;
(Continued)

(56) References Cited

U.S. PATENT DOCUMENTS

2009/0054846 A1    2/2009  Moser et al.
2009/0054850 A1*   2/2009  Moser ............... A61M 5/31535
                                                                604/208

FOREIGN PATENT DOCUMENTS

CN    101370542    2/2009
CN    102083489    6/2011
(Continued)

OTHER PUBLICATIONS

WO 2012049141A1, Butler et al., publication date: Apr. 19, 2012.*
(Continued)

*Primary Examiner* — Manuel Mendez
(74) *Attorney, Agent, or Firm* — Fish & Richardson P.C.

(57) ABSTRACT

A drug delivery device for selecting and dispensing a number of user variable doses of a medicament includes a dose limiter for preventing the setting of a dose exceeding an amount of liquid left in a cartridge of the drug delivery device. The device includes a housing, a dose selector for selecting a dose by rotation relative to the housing, a dosing element, and a releasable clutch for rotationally coupling the dosing element to the dose selector during dose selecting and for rotationally decoupling the dosing element from the dose selector during dose dispensing. The clutch includes a male spline, a corresponding female spline and a curved or inclined surface which is orientated such that re-engagement of the clutch guides the male spline into a predefined rotational orientation with respect to the female spline.

20 Claims, 6 Drawing Sheets

(52) U.S. Cl.
CPC .... *A61M 5/31548* (2013.01); *A61M 5/31553* (2013.01); *A61M 5/31578* (2013.01); *A61M 5/31593* (2013.01); *A61M 2005/2403* (2013.01); *A61M 2005/3126* (2013.01)

(58) Field of Classification Search
CPC .......... A61M 5/31578; A61M 5/31593; A61M 2005/2403; A61M 2005/3126
USPC ......... 604/211, 208, 218–231, 506, 207–209
See application file for complete search history.

(56) References Cited

FOREIGN PATENT DOCUMENTS

| JP | 2006-519074 | 8/2006 |
|---|---|---|
| JP | 2013-506451 | 2/2013 |
| WO | WO 2004/078239 | 9/2004 |
| WO | WO 2009/132778 | 11/2009 |
| WO | WO 2011/039212 | 4/2011 |
| WO | WO 2011/068531 | 6/2011 |
| WO | WO 2012/049140 | 4/2012 |
| WO | WO 2012/049141 | 4/2012 |

OTHER PUBLICATIONS

International Search Report and Written Opinion in International Application No. PCT/EP2014/065341 dated Jan. 22, 2015, 10 pages.
International Preliminary Report on Patentability Chapter I in International Application No. PCT/EP2014/065341 dated Jan. 19, 2016, 7 pages.
Rote Liste, "50. Hypophyses-, Hypothalamushormone, andere regulatorische Peptide u. ihre Hemmstoffe," Chapter 50, ed. 2008, 20 pages.

* cited by examiner

DRUG DELIVERY DEVICE

CROSS-REFERENCE TO RELATED APPLICATIONS

This application is a U.S. national stage application under 35 USC § 371 of International Application No. PCT/EP2014/065341, filed on Jul. 17, 2014, which claims priority to European Patent Application No. 13176886.3, filed on Jul. 17, 2013, the entire contents of which are incorporated herein by reference.

TECHNICAL FIELD

The present disclosure is generally directed to drug delivery devices for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. Some aspects of the present invention are not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Some aspects of the present invention are applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some aspects of the present invention are applicable for all of these types of devices, i.e. for devices with or without a drive spring.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

The dosing section of drug delivery devices for selecting and dispensing a number of user variable doses of a medicament often comprises a display for indicating the selected dose to a user. This is especially important where a user may select a different dose each time depending on the state of health. There are mechanical displays, e.g. a drum with printed numbers on its outer surface, wherein the number corresponding to the actually selected dose is visible through a window or opening in the device. Although such mechanical displays are simple and reliable, they usually require a relatively large construction space which makes the devices bulky. In addition, the size of the numbers is in some cases too small for visually impaired users. Further, electronic displays are known, e.g. LCD displays, which have the benefit of a relatively large number size without requiring too much construction space. However, a downside of electronic displays is that they require an energy source and that such electronic components may be too expensive, especially in a disposable drug delivery device.

It might be desirable designing the housing of the drug delivery device with a non-circular cross-section for example to avoid a bulky appearance of the device, to improve handling due to the non-cylindrical body shape, to reduce the probability of the device rolling from an elevated surface such as a table or shelf and becoming damaged, or to increase differentiation relative to other drug delivery devices. An example of such a non-cylindrical body shape is given in EP 1 414 507 B1, where parts of the housing are oval whereas a dose selector knob is cylindrical.

To prevent the user from accidentally interfering with the dosage selector during the injection and either preventing injection or changing the dialled dose, many injector devices disengage the dosage selector from the drive mechanism during injection. In this case the dosage selector may become locked in place or may rotate freely and not impact on the process of injection. Where the dosage selector is disengaged from the mechanism it is generally regarded as not important as to what orientation the dosage selector is in when it is reengaged to the driving mechanism.

In the case of non-axisymmetric devices or with devices which have a definite home position marked on the dosage selector, it may be desirable that the dosage selector is correctly realigned to the housing when the injection button is released. If the dosage selector is not aligned to the housing, the user may think that the device looks unsightly or may even interpret the misalignment as a mechanical problem. Further, the device might not fit into pockets, bags or carry cases or debris could become trapped between the misaligned faces.

SUMMARY

Certain aspects of the present invention provide for drug delivery devices which allow realignment of the dosage selectors.

In more detail, this disclosure describes a drug delivery device comprising a housing, a dose selector for selecting a dose by rotation relative to the housing, a dosing element and a releasable clutch for rotationally coupling the dosing element to the dose selector during dose selecting and for rotationally decoupling the dosing element from the dose selector during dose dispensing.

According to a first embodiment of the present invention, this object is solved by a drug delivery device for selecting and dispensing a number of user variable doses of a medicament comprising a housing defining a longitudinal axis, a dose selector for selecting a dose by rotation relative to the housing, a dosing element, and a releasable clutch for rotationally coupling the dosing element to the dose selector during dose selecting and for rotationally decoupling the dosing element from the dose selector during dose dispensing. The clutch comprises at least one male spline, at least one corresponding female spline and at least one curved or inclined surface which is orientated with respect to the longitudinal axis such that re-engagement of the clutch guides the at least one male spline into a predefined rotational orientation with respect to the at least one female spline. In other words, re-engagement of the clutch brings the dose selector back into a start position relative to the housing and thus realigns the device. This position may be defined by a non-axisymmetric design of the device or by a marking on the dosage selector and/or the housing.

For example, when the user releases the injection button, the dosing element may move axially back to its "0" or home position. As the dosing element comes in to contact with the dosage selector, e.g. male location features on the dosing element begin to engage with corresponding female helical features located within the dosage selector. This causes the dosage selector to rotate until it becomes fully engaged with the dosing element. The dosage selector is then fully aligned with the device housing. Because the dosing element and the dose selector are rotationally decoupled during dose dispensing, the dose selector may or may not be misaligned during dose dispensing. Thus, if the dose selector is already in a position where the male and female splines match, no further rotation occurs at the end of dose dispensing and the clutch simply re-engages.

There may be more than one suitable 'home' position. For example, if the device has a broadly triangular cross-section, the dose selector could be realigned with the housing in any one of three positions.

Preferably, the curved or inclined surface is a helical surface for guiding the dosing element and the dose selector in a defined rotational orientation as they move axially with respect to each other during re-engagement of the clutch. As an alternative, the at least one male spline and/or the at least one female spline may be tapered or wedge-shaped. Further configurations of the curved or inclined surface are possible as long as the relative axial movement of the dosing element and the dose selector is transmitted or initiates a rotational movement component realigning these two components such that the male and female splines match and fit into each other.

The at least one male spline and the at least one female spline may extend basically parallel to the longitudinal axis. In other words, a relative axial movement of the dosing element and the dose selector causes engagement of the spines provided that they are aligned.

Irrespective of the above features, it is a basic concept of some aspects of the present invention to provide a non-axisymmetric drug delivery device, wherein the housing and the dose selector each have a non-circular cross-section, at least in a region where the housing abuts the dose selector. Preferably, the housing and the dose selector both have the same, non-circular cross-section, at least in a region where the housing abuts the dose selector. The housing and the dose selector may or may not actually abut. Rather, a small gap may be provided between the housing and the dose selector to reduce friction during relative rotation of these components. For example, a triangular shape of the device is considered very comfortable for many users, especially for users with impaired dexterity.

Preferably, the dosing element rotates relative to the dose selector during dose dispensing, wherein at the end of dose dispensing the dosing element is in a predefined rotational orientation relative to the housing. Thus, the position of the dosing element within the housing may be used to bring the dose selector in the desired rotational position with respect to the housing as the clutch re-engages the dosing element and the dose selector.

The dose limiter according to certain aspects of the present invention may be used in various types of drug delivery devices including disposable and reusable devices and devices with or without a driving spring. According to a preferred embodiment the drug delivery device comprises a cartridge holder for retaining the cartridge, a piston rod displaceable relative to the cartridge holder, a driver coupled to the piston rod and at least one clutch, wherein the clutch decouples the driver and the dosing element during dose selecting and couples the driver and the dosing element during dose dispensing. The drug delivery device may further comprise a spring driving the dosing element during dose dispensing.

A preferred embodiment of the invention comprises a drug delivery device with a display for indicating the selected dose, wherein the display comprises at least one belt having symbols for indicating the selected dose and being coupled to the dosing element such that a rotation of the dosing element spools the belt. This allows a relatively large sized indication of the set dose in a compact construction space. Especially in a non-axisymmetric, for example triangular, design of the housing the belt may be guided on a flat or slightly curved guiding face which results in less distortion due to flatter number display mechanism which in turn enables a higher display magnification compared to cylindrical concepts.

The dosing element may be any suitable component part of the drug delivery device which performs a rotational movement both during dose setting, i.e. increasing or decreasing the selected dose, and during dose dispensing. This results in the dose indication belt being spooled not only during dose setting but also during dose dispensing such that, after dispensing the whole or a portion of a set dose, the display indicates the remainder of the set dose, which will be zero if the whole dose has been dispensed. Although it is preferred if the dosing element performs a pure rotational movement during dose setting and dose dispensing, i.e. not a combined axial and rotational movement, it is also possible to drive the belt with a dosing element which travels on a helical path during dose setting and/or dose dispensing. The term dosing element is not intended to limit said element to a component which has the sole or main function to select a dose. Moreover, any component part rotating during dose setting and dose dispensing may be the dosing element, even if its main function is e.g. to drive the piston rod, to strain a spring, to transfer a movement from one component part to another, or the like. The dosing element may be a single component part or may comprise two or more components which are e.g. rotationally constrained.

Preferably, the dosing element rotates in a first direction during dose selecting and rotates in a second, opposite direction during dose dispensing. Thus, de-coupling the dosing element and the last dose sleeve during dose dispensing prevents the dose limiter being actuated during dose dispensing. In other words, only an increase in dose selection is blocked by the dose limiter, whereas it is possible to fully dispense any dose selected even when the dose limiter prevents setting of a higher dose.

In a further embodiment the drug delivery device comprises a dose limiter for preventing the setting of a dose, which exceeds the amount of liquid left in a cartridge of the drug delivery device. Preferably, the dose limiter comprises a last dose nut coupled to the dosing element during dose selecting such that rotation of the dosing element causes an axial movement of the last dose nut, and a stop element, which blocks further movement of the last dose nut, if a dose is selected corresponding to the amount of liquid left in the cartridge. The dose limiter may further comprise a last dose sleeve rotationally coupled to the dosing element during dose selecting and rotationally de-coupled from the dosing element during dose dispensing, wherein the last dose nut is coupled to the dosing element by the last dose sleeve.

A preferred embodiment of the invention comprises a drug delivery device with a (further) nut coupled to the dosing element such that rotation of the dosing element causes an axial movement of the nut in a direction opposite to the direction of the axial movement of the last dose nut. In other words, upon rotation of the dosing element the nut and the last dose nut are both moved axially, however in opposite directions. Preferably, the nut approaches the last dose nut as they are moved axially. Abutment or contact of the nut with the last dose nut may be used to activate the limiter mechanism if a dose is selected corresponding to the amount of liquid left in the cartridge.

The last dose nut may be a full nut or a half nut. Preferably, the last dose nut is a ring or sleeve-like component. The transmission of the rotation of the dosing element into an axial movement of the last dose nut may be achieved by a thread. For the function of the dose limiter of certain aspects of the present invention, the last dose nut may either perform a mere axial movement or a combined axial and rotational movement, e.g. on a helical path.

Preferably, the last dose nut engages the stop element on the dosing element when the nut contacts the last dose nut. When there are less than e.g. 120 IU of insulin formulation remaining in the cartridge the last dose protection nut may become engaged with the restriction nut forming a rotary or an axial hard stop with the dosing element.

Preferably, the further nut has an additional function in the device. For example, the nut may comprise rotational hard stops and the dosing element may comprise corresponding rotational stops interacting with the rotational hard stops of the nut for limiting axial movement of the nut. Thus, the nut acts as a restriction nut limiting the minimum settable dose (zero IU of insulin formulation) and the maximum settable dose (e.g. 120 IU of insulin formulation).

According to an embodiment of the invention the dosing element comprises a drive sleeve, which has a flange with clutch teeth for coupling the drive sleeve to corresponding teeth of the last dose sleeve, and a transfer sleeve, which is rotationally constrained to the drive sleeve and comprises the stop element. A limited axial movement of the drive sleeve relative to the transfer sleeve may be allowed, e.g. for coupling and de-coupling the clutch teeth.

An example of transferring the rotational movement of the dosing element into an axial movement component involves a threaded engagement. Preferably, the nut comprises a thread engaging a thread on the transfer sleeve. In addition, the last dose nut may comprise a thread engaging a thread of the last dose sleeve.

To allow axial movement of the nut and/or the last dose nut but to prevent relative rotation with respect to a component like the housing of the device, a splined engagement may be provided. Preferably, a housing or chassis is rotationally constrained to the last dose nut and/or the nut. The chassis or housing may include a rib, a bar or a finger to guide the last dose nut and/or the nut.

Preferably, the cartridge contains a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—

(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned poly-saccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immuno-globulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intra-chain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Exemplary embodiments of the invention will now be described with reference to the accompanying drawings, in which:

FIGS. 5a, b show cut-away views of a further detail of the drug delivery device of FIG. 1;
FIG. 6 shows a cut-away view of a further detail of the drug delivery device of FIG. 1;
FIG. 7b shows a sectional view of the detail of FIG. 7a.

DETAILED DESCRIPTION

Figure 1:
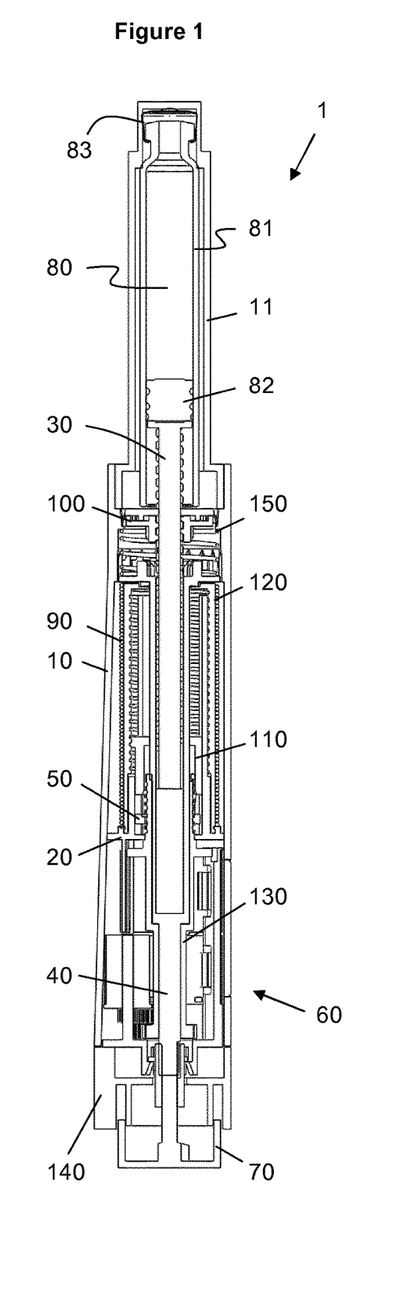
FIG. 1 shows a sectional view of a drug delivery device.
Figure 2:
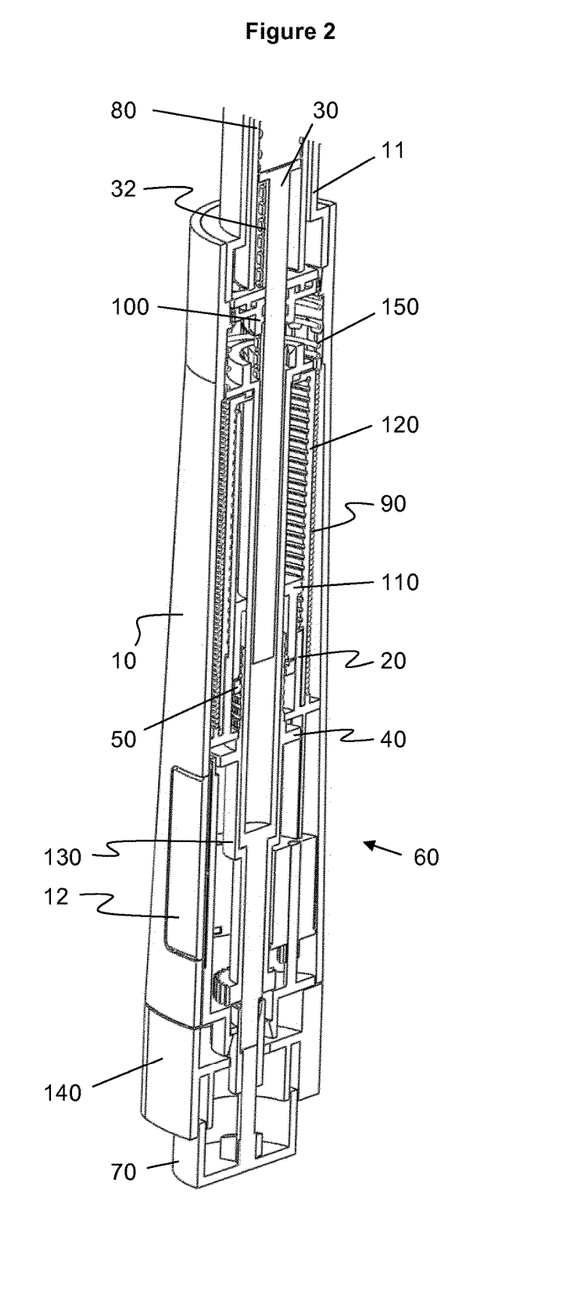
FIG. 2 shows a cut-away view of a drug delivery device of FIG. 1.
Figure 3:
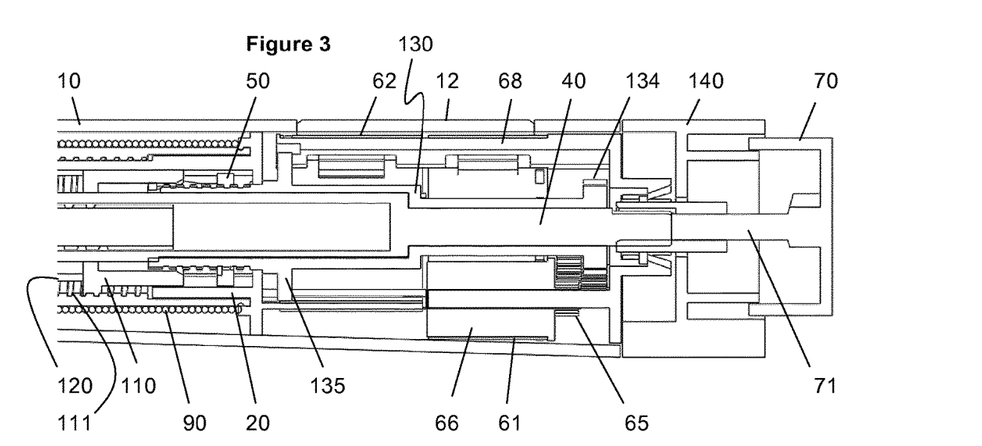
FIG. 3 shows an enlarged detail of FIG. 1.

FIG. 1 shows a drug delivery device 1 in the form of an injection pen. The device has a distal end (upper end in FIG. 1) and a proximal end (lower end in FIG. 1). The component parts of the drug delivery device 1 are shown in FIGS. 2 and 3 in more detail. The drug delivery device 1 comprises an outer housing 10, an inner body or chassis 20, a piston rod 30, a driver 40, a nut 50, a display 60, a button 70, a cartridge 80, a torsion spring 90, a drive nut 100, a last dose nut 110, a last dose sleeve 120, a transfer sleeve 130, a dose selector 140 and a return spring 150. A needle arrangement (not shown) with a needle hub and a needle cover may be provided as additional components, which can be exchanged as explained above.

The outer housing 10 is a generally tubular element having a distal part, which forms a cartridge holder 11 for receiving cartridge 80, and a proximal part for receiving the dosing mechanism. In a preferred embodiment, the outer housing 10 has a circular cross-section in the region of the cartridge holder 11 and in the intermediate region where the cartridge holder merges with the outer housing part covering the dosing mechanism, whereas the proximal region of the housing 10 has a triangular cross-section. Thus, it is comfortable to hold and handle the device 1. A window 12 is provided in the outer housing 10 allowing to view a detail of the display 60. The cartridge holder 11 may be a single-component part with the outer housing 10 or a separate component part attached to the outer housing 10 during assembly. As explained below in more detail, a portion of the outer housing 10 is provided with radially inwardly orientated teeth 13 forming a clutch with driver 40.

The chassis 20 is a generally tubular element which is axially and rotationally fixed within the outer housing 10. A flange may be provided attach a fee end of spring 90.

The piston rod 30 is an elongate element having an external thread 31 which is engages the drive nut 100. Further, the piston rod comprises a spline 32 or the like alignment means for rotationally coupling the piston rod 30 in the outer housing 10 but allowing axial displacement of the piston rod 30 relative to the outer housing 10. A bearing 33 is provided at the distal end of piston rod 30.

The driver 40 has a generally tubular distal portion which at least partly surrounds the piston rod 30. A proximal portion of the driver may have a smaller diameter. This proximal portion is a solid bar in the embodiment depicted in the figures but may as well be tubular. A flange 41 is provided at the distal end of the driver 40. As will be explained below in more detail, the flange comprises distally orientated teeth 42 forming a clutch which couples or decouples the driver to the drive nut 100. Further teeth 43 are provided on the proximal face of the flange 41 which are part of a clutch which couples or decouples the driver to the last dose sleeve 120. The driver 40 is splined to the transfer sleeve 130 to prevent relative rotation.

Figure 4:
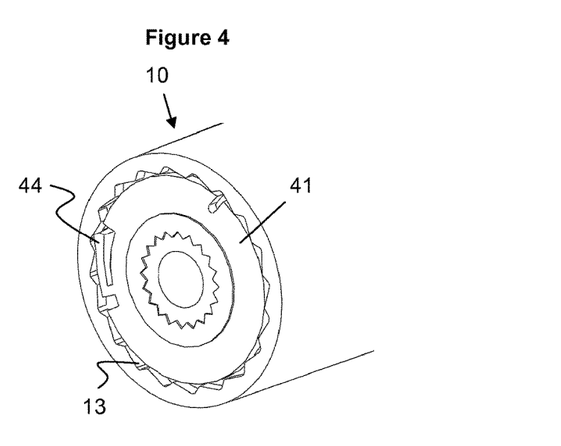
FIG. 4 shows a sectional view of a detail of the drug delivery device of FIG. 1.

In addition, a clutch is provided between the radially outer surface of flange 41 and outer housing 10. As shown in FIG. 4, this clutch may be formed as a ratchet with a ratchet finger 44 on the driver 40 and teeth 13 on an inner surface of the outer housing 10. The clutch allows stepwise rotation in a first direction during dose setting (dose increasing) but is designed to withstand the torque of torsion spring 90. The clutch is designed such that a user can overcome the clutch, i.e. reduce a set dose such that finger 44 overrides teeth 13 in a rotation opposite the first direction.

The nut 50 is provided between the transfer sleeve 130 and the chassis 20. External ribs of the nut 50 engage inner splines of the chassis 20. An internal thread of the nut 50 engages an external thread of the transfer sleeve 130. As an alternative, splines and ribs could be provided on the interface between the nut 50 and the transfer sleeve 130 and threads could be provided on the interface between the nut 50 and the chassis 20. As a further alternative, the nut 50 may be designed as e.g. a half nut. Further, in the embodiment of FIGS. 5*a*, 5*b* and 11, rotational hard stops 51, 52 are provided on nut 50 for interaction with corresponding stops on the transfer sleeve 130.

Figure 8:
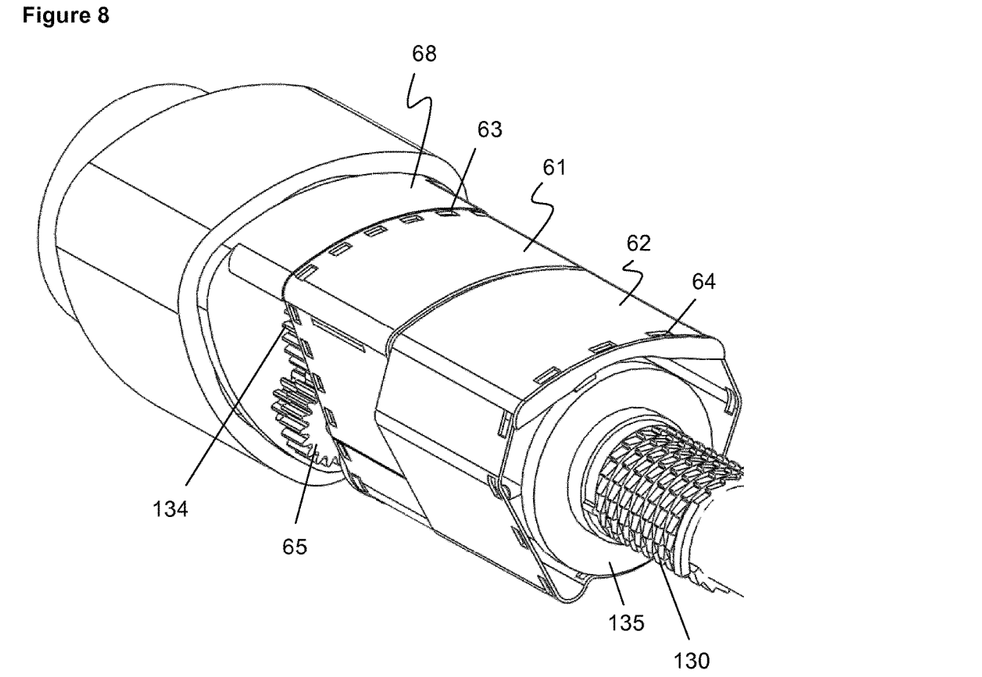
FIG. 8 shows a cut-away view of the display of the drug delivery device of FIG. 1.
Figure 9:
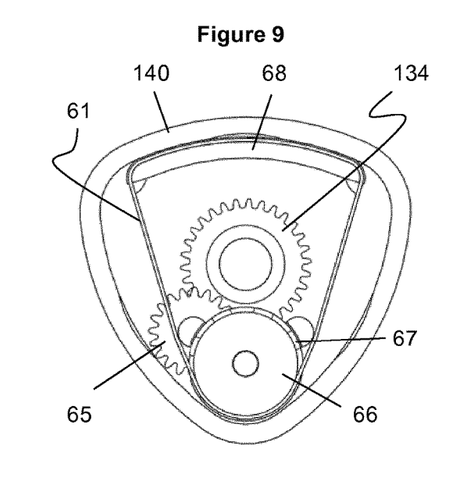
FIG. 9 shows a sectional view of the display of FIG. 8.
Figure 10:
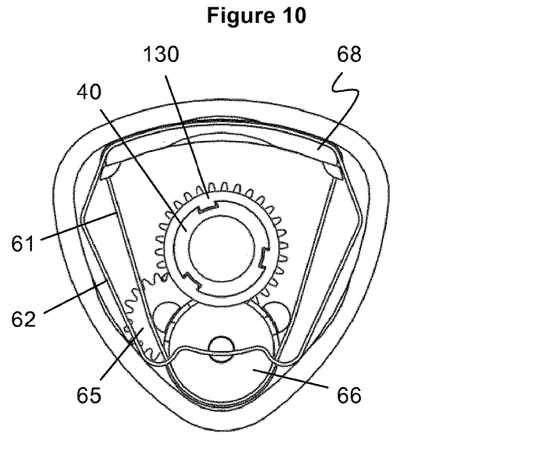
FIG. 10 shows a sectional view of the display of FIG. 8.

The display 60 comprises in the embodiment shown in FIGS. 8 to 10 a first belt 61 and a second belt 62 each having a series of numbers or the like symbols thereon and each having a series of apertures 63 and 64, respectively, which are arranged in uniform distribution with equal distance between the apertures. However, the size and/or the distances between apertures 63 and between apertures 64 may be different. The first belt 61 is driven via a drive gear 134 provided on the transfer sleeve 130, a transfer gear set 65, having two rotationally coupled gear wheels, and a transfer gear and sprocket set 66. A first gear wheel of the transfer gear set 65 meshes with the drive gear 134 and the second gear wheel of the transfer gear set 65 meshes with a transfer gear wheel of the transfer gear and sprocket set 66, which further comprises a sprocket rotationally coupled to the transfer gear wheel and engaging with protrusions 67 the apertures 63 of the first belt. Thus, rotation of the transfer sleeve 130 spools the first belt 61. The second belt 62 is driven by a sprocket 135 of the transfer sleeve 130 which has in the embodiment shown in the Figures two protrusions 136 engaging the apertures 64 in the second belt 62. Thus, the second belt 62 is directly coupled to the transfer sleeve 130. As the distance between protrusions 136 is much bigger than the distance between apertures 64, a continuous rotation of the transfer sleeve 130 is translated into an intermittent motion of the second belt 62.

Both belts 61, 62 are guided on a striker plate 68 which is fixed within the outer housing 10. The striker plate 68 has a flat or arched surface such that the part of the belts guided on the striker plate 68 has a curvature which is lower than the curvature of the cylindrical portion of the outer housing 10. Due to the striker plate 68, the outer housing 10 has its (rounded) triangular shape as indicated in FIGS. 9 and 10. In the embodiment depicted in the Figures, the first belt 61 is guided by the striker plate 68 and the sprocket of the transfer gear and sprocket set 66 on a generally triangular closed loop. The second belt may further be guided by suitable means to form a folded closed loop as indicated in FIGS. 8 and 10.

The button 70 forms the proximal end of the device and is held within dose selector 140 to allow relative rotation to the dose selector 140 and limited axial movement. A centrally locates stem 71 abuts with its distal end face the proximal end face of the proximal part of driver 40. Thus, axial movement of button 70 is directly transferred to driver 40.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal band 83 is used to hold the rubber seal in place. The cartridge 80 is provided within the cartridge holder 11 with bearing 33 of piston rod 30 abutting bung 82.

The drug delivery device 1 is intended to accept a 1.5 mL cartridge or a 3.0 mL cartridge, but the design could be adapted to accept other medicament container sizes or formats. The embodiment of the device depicted in the Figures is designed to be disposable in that the cartridge 80 cannot be replaced by the user or healthcare professional. A reusable variant of the device would involve making the cartridge holder removable and allowing the resetting of the piston rod 30.

The torsion spring 90 has two free ends, wherein the distal end is attached to the flange 41 of the driver 40 and the proximal end is attached to a flange of the stationary chassis 20. Thus, rotation of the driver 40 relative to the chassis 20 strains the torsion spring 90 and the stored energy may be released by allowing the driver 40 to rotate relative to the chassis 20. The torsion spring 20 may be assembled in a pre-strained state to provide sufficient torque even for dispensing small doses. In an alternative embodiment the spring may be pre-charged such that the stored energy is sufficient to dispense the whole contents of a full cartridge.

The drive nut 100 is a sleeve-like or disk-shaped component which has an inner thread engaging the thread 31 of the piston rod 30. The drive nut 100 is held within the outer housing 10 such that the drive nut 100 is allowed to freely rotate. In the embodiment shown in the Figures, the drive nut 100 comprises a flange 101 which forms a contact surface for the return spring 150 which is interposed between the driver 40 and the drive nut 100. Further, teeth 102 are provided for engagement with teeth 42 of driver 40.

The last dose nut 110 is provided interposed between the driver 40 and the chassis finger 21. A splined engagement between the chassis finger 21 and the drive nut 110 allows axial movement of the last dose nut 110 but prevents relative rotation with respect to the chassis 20. The last dose nut is provided with an outer thread 111.

The last dose sleeve 120 cooperates with the last dose nut 110 and nut 50 to form a last dose mechanism preventing setting of a dose which increases the amount of liquid left in the cartridge 80. The last dose sleeve 120 is a hollow component having an internal thread 121 which engages outer thread 111 of the last dose nut 110. A distal end face of the last dose sleeve 120 is provided with teeth 122 interacting with the teeth 43 provided on the proximal face of the flange 41 for rotationally coupling the last dose sleeve 120 to the driver 40.

The transfer sleeve 130 is a tubular element which is splined to the driver 40 such that it is rotationally constrained to the driver 40 but allows relative axial movement with respect to the driver. As mentioned above, the transfer sleeve 130 has a distal portion provided with thread 131 and rotational stops 132, 133. Further, the transfer sleeve 130 is provided with gear 134 for driving the first belt 61 and a sprocket 135 for driving the second belt 62. A stepped portion of the transfer sleeve 130 corresponds to the change in diameter of the driver 40 such that axial movement of the driver 40 relative to the transfer sleeve 130 is limited in the proximal direction.

Figure 14:
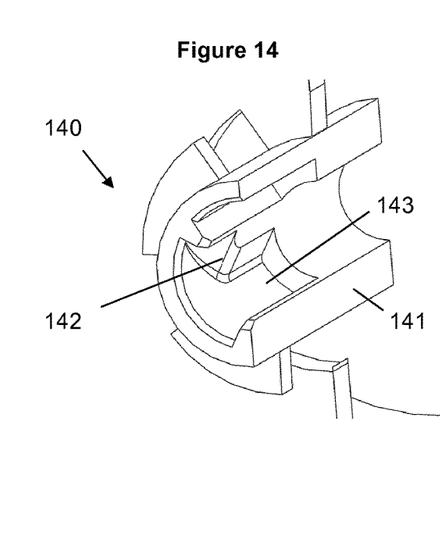
FIG. 14 shows a cut-away view of a detail of the drug delivery device of FIG. 1.
Figure 15:
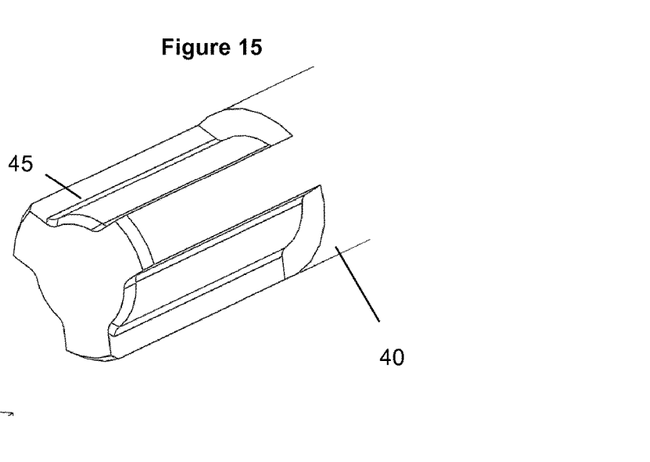
FIG. 15 shows a perspective view of a detail of the drug delivery device of FIG. 1.

The dose selector 140 has a triangular outer shape which corresponds to the outer shape of the proximal part of the outer housing 10. The dose selector 140 comprises an inner sleeve 141 guiding the stem 71 of the button 70 and receiving the proximal end of driver 40. As depicted in FIGS. 14 and 15 the proximal end of driver 40 has splines 45 engaging an inner guiding contour of the dose selector. This guiding contour includes a helical surface 142 and a female spline 143, wherein the helical surface 142 is arranged such that a relative axial movement of the driver 40 with respect to dose selector 140 results in an alignment of the male splines 45 with respect to the female splines 143. Thus, the dose selector 140 is rotated with respect to the driver 40.

The return spring 150 is a compression spring which is located between flange 101 of drive nut 100 and flange 41 of driver 40. Thus, return spring 150 urges the driver 40 in the proximal direction. If button 70 is pushed by a user, driver 40 is moved in the distal direction against the bias of return spring 150.

In the following, the function of the disposable drug delivery device 1 and its components will be explained in more detail.

To use the device, a user has to select a dose. In the start (at rest) condition as shown in FIGS. 1 to 3 and 16*a* to 16*c* the torsion spring 90 has enough preload such that if the user selects the minimum dose the device will be able to deliver that minimum dose. At rest the dose indicator belts 61, 62 display 0 or the equivalent marking to show that no dose has been selected.

A priming and/or safety shots may be required prior to an injection. Priming is the act of preparing the device for first use. In existing pen injectors this means setting and delivering one or more small doses into air so that the 'play' (any clearances) and tolerances in the device are removed and that components are placed into suitable compression or tension. Safety shots are where the user sets and delivers one or more small doses into air before each injection to ensure that the needle is not blocked.

The user sets a dose by rotating the dose selector 140. Rotating the dose selector 140 rotates the driver 40 and adds preload to the torsion spring 90. The transfer sleeve 130 is splined to the driver 40 and indexes the dose number mechanism of display 60 when the user dials the dose selector 140.

FIG. 4 shows the ratchet features 41 on the driver 40 that engage with splines 13 on the internal surface of the outer housing 10 to prevent the dose selector 140 rotating back to its initial position due to the torsion spring torque. These ratchet features 13, 41 become disengaged when the user fully depresses the injection button 70.

Figures 5A, 5B, 6:
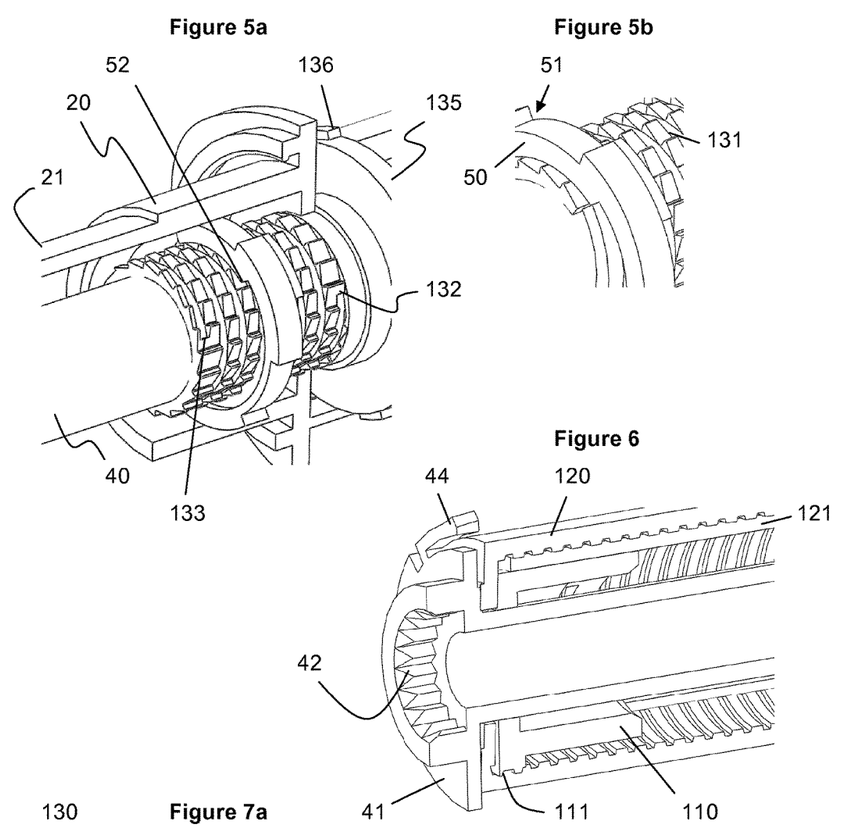

Limits for a minimum dose (0 IU) and a maximum dose (e.g. 120 IU) are provided by hard stop features on the nut 50 which interfere with features 132, 133 on the transfer sleeve 130 and therefore prevent further relative rotation. FIGS. 5*a* and 5*b* show the nut 50 in an intermediate position, i.e. with about 60 IU dialled.

Figure 7A:
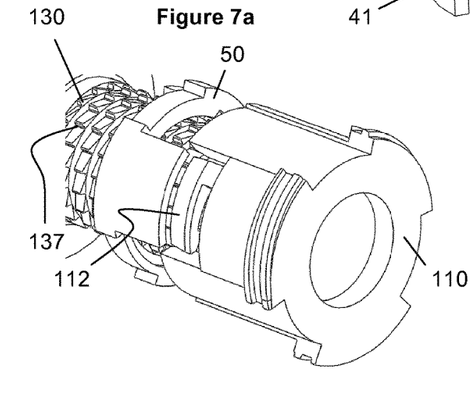
FIG. 7a shows a cut-away view of a detail of the drug delivery device of FIG. 1.
Figure 7B:
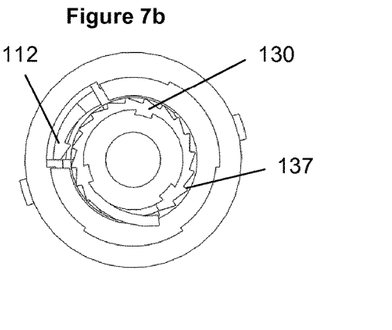

A last dose protection prevents the user from setting a dose greater than the available volume in the cartridge 80. During dose setting, the driver 40 is engaged with the last dose sleeve 120 via teeth 43 and 122. When the cartridge volume falls below 120 units the last dose nut 110 has moved in to a position where it can interfere with the nut 50. When the user attempts to dial a dose greater than that remaining, the nut 50 bends a flexible feature on the last dose nut 110 such that it engages with step-like spline features 137 on the transfer sleeve 130 to form a rotary hard stop. FIGS. 7*a* and 7*b* show the device shortly before engagement of this last dose mechanism.

The dose number is increased or reduced as the dose selector 140 is rotated. This is achieved via a spur gear feature 134 within the transfer sleeve 130 engaging with a gearbox 65 to a sprocket 66 which indexes the corresponding number belt 61. The second number belt 62 may be indexed by coupling a secondary feature (protrusion 136) on the transfer sleeve 130 to an additional gearbox or directly to the second belt 62. In the embodiment shown in FIGS. 8 to 10, the first number belt 61 may be provided with numbers "0" to "9" twice, and the second number belt 62 may have the numbers "0" to "12" thereon. Instead of the "0" on the second belt 62, a blank may be provided. In other words, for every full rotation of dose selector 140 the first belt 61 (the single units counter belt) makes a full revolution displaying the numbers "0" to "9" twice. At the same time, the second belt 62 (ten units counter belt) intermittently moves by two position, i.e. for example from blank to "1" and from "1" to "2". Starting from zero units dialled, a full revolution of dose selector 140 will result in a display showing "2" on the second belt 62 and "0" on the first belt 61, such that belts 61 and 62 together display "20".

Figure 16A:
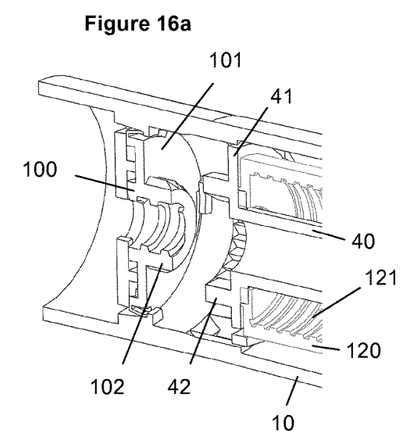
FIGS. 16a-c show cut-away views of details of the drug delivery device of FIG. 1 during dose setting.
Figure 16B:
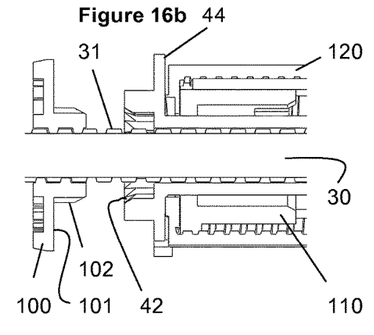
Figure 16C:
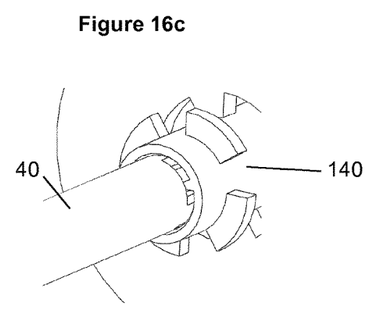
Figure 17A:
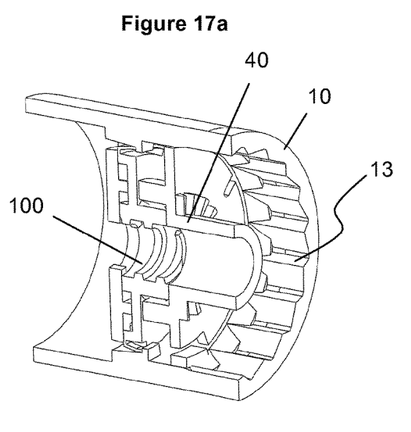
FIGS. 17a-c show cut-away views of details of the drug delivery device of FIG. 1 during dose dispensing.
Figure 17B:
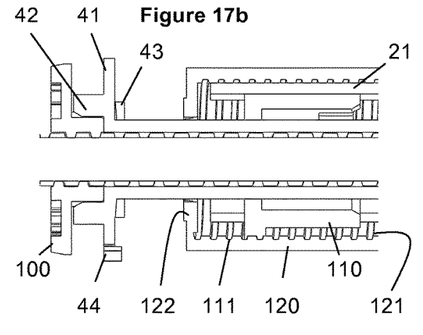
Figure 17C:
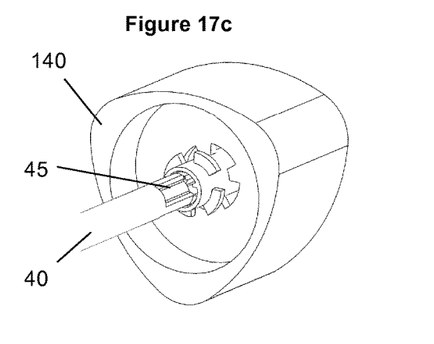

When the injection button 70 is pressed the following actions take place which can be understood comparing FIGS. 16*a* to 16*c* (button 70 released) with FIGS. 17*a* to 17*c* (button 70 pressed):

The driver 40 is moved forward by the injection button 70 and disengages from the last dose sleeve 120. The last dose protection nut 110 thus remains static throughout an injection. Further, the driver 40 begins to compress the return spring 150 and engages with the lead screw drive nut 100 via clutch teeth 42, 102. At this point the driver 40 is still engaged with the energy storage ratchet 13, 41 to prevent the torsion spring 90 from unwinding. The driver 40 disengages from the dose selector 140 which may now be rotated freely without influencing injection or dial dose. Over the last 1 mm or so the driver 40 becomes fully engaged with the drive nut 100 and moves off the energy storage ratchet 13, 41. The torsion spring 90 begins to unwind rotating the driver 40 which in turn spins the drive nut 100. As the drive nut 100 rotates the piston rod 30 (lead screw), which is splined to the device outer housing 10, moves forwards dispensing the medication.

Dose interruption and dose splitting is possible. If the axial force on the injection button 70 is removed, the button 70 returns to its initial axial position relative to the dose selector 140 under the action of return spring 150. This allows the ratchets 41 on the driver 40 to engage with the splines 13 of the outer housing 10, thus preventing further injection due to the driving torque of the torsion spring 90. Further, this reengages the driver 40 with the dose selector 140 and the last dose sleeve 120, thus allowing the dose selector 140 to rotate again. At this point the dose selector 140 will realign with the outer housing 10 as explained below. The dose can be changed by rotating the dose selector 140 and pressing the button 70 restarts the injection manoeuvre.

Figure 11:
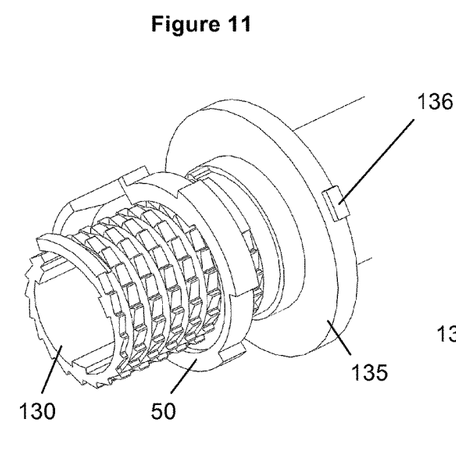
FIG. 11 shows a cut-away view of a further detail of the drug delivery device of FIG. 1.
Figure 12:
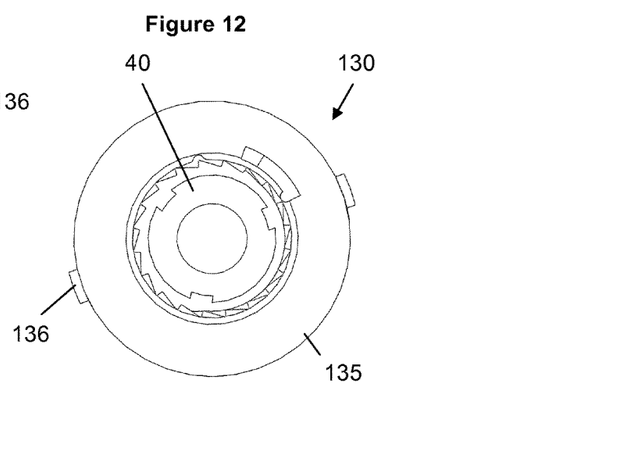
FIG. 12 shows a sectional view of the detail of FIG. 11.

During injection the torsion spring 90 will unwind, rotating the driver 40. This will index the dose number mechanism such that the number counts down towards "0". At the same time the nut 50 move back towards its "0" position. When the nut 50 has reached this position the user will hear and possibly feel a "click" to signify end of dose. This is achieved by features on both the nut 40 and the transfer sleeve 130 passing over each other with slight detent interference as shown in FIGS. 11 and 12.

Figure 13A:
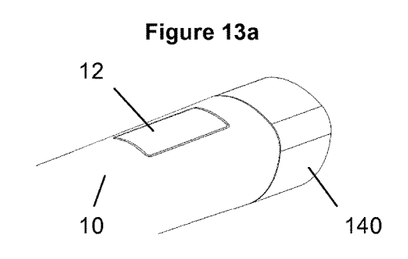
FIGS. 13a, b show perspective views of the proximal end of the drug delivery device of FIG. 1 in different positions.
Figure 13B:
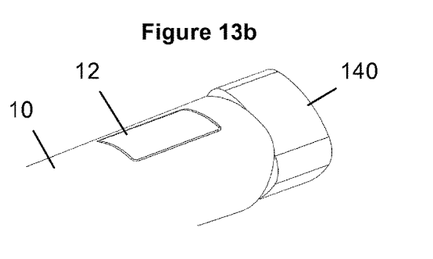

This exemplary embodiment has a triangular, i.e. non-axisymmetric, outer housing 10 and dose selector 140 which means that the dose selector 140 becomes 'misaligned' relative to the outer housing 10 during dose setting. FIGS. 13a and 13b show the dose selector 140 aligned and misaligned, respectively. There is no technical problem with this but users may prefer that the dose selector 140 is realigned to the outer housing 10 at the end of each injection. Therefore the device includes a mechanism for realigning the dose selector 140 with the device outer housing 10 when the user releases the button 70.

FIG. 3 shows that stem 71 of injection button 70 abuts the proximal end face of driver 40. Thus, if button 70 is pushed during dose dispensing driver 40 is axially advanced with respect to dose selector 140 such that splines 45 of the driver disengage from splines 143 of the dose selector 140. With the button 70 pressed and the driver disengaged, the dose selector 140 free-wheels with respect to the housing 10 and driver 40. As depicted in FIGS. 14 and 15, when the user releases the button 70, the driver 40 moves axially back to its "0" position. As the driver 40 comes in to contact with the dose selector 140, splines 45 which form male location features on the driver 40 begin to engage with helical features 142 located within the dose selector 140. This causes the dose selector 140 to rotate until it becomes fully aligned with the outer housing 10. In this aligned position, splines 45 enter into corresponding female splines 143 as the driver 40 is further pushed in the proximal direction which rotationally constrains dose selector 140 and driver 40.

The invention claimed is:

1. A drug delivery device for selecting and dispensing a number of user variable doses of a medicament, the drug delivery device comprising:
   a housing defining a longitudinal axis;
   a dose selector for selecting a dose by rotation of the dose selector relative to the housing;
   a dosing element; and
   a releasable clutch configured to rotationally couple the dosing element to the dose selector during dose selecting and to rotationally decouple the dosing element from the dose selector during dose dispensing,
   wherein the clutch comprises at least one male spline, at least one corresponding female spline and at least one curved or inclined surface oriented with respect to the longitudinal axis such that re-engagement of the clutch guides the at least one male spline into a predefined rotational orientation with respect to the at least one female spline.

2. The drug delivery device of claim 1, wherein the surface is a helical surface.

3. The drug delivery device of claim 1, wherein at least one of the at least one male spline or the at least one female spline is tapered or wedge-shaped.

4. The drug delivery device of claim 1, wherein the at least one male spline and the at least one female spline extend parallel to the longitudinal axis.

5. The drug delivery device of claim 1, wherein the housing and the dose selector each has a non-circular cross-section at least in a region where the housing abuts the dose selector.

6. The drug delivery device of claim 5, wherein the non-circular cross section of the housing corresponds to the non-circular cross-section of the dose selector at least in a region where the housing abuts the dose selector.

7. The drug delivery device of claim 1, wherein during the dose dispensing the dosing element rotates relative to the dose selector, and at an end of the dose dispensing the dosing element is in a predefined rotational orientation relative to the housing.

8. The drug delivery device of claim 1, further comprising:
   a cartridge holder for retaining a cartridge containing the medicament;
   a piston rod displaceable relative to the cartridge holder; and
   a driver coupled to the piston rod and at least one clutch, wherein the clutch is configured to decouple the driver and the dosing element during the dose selecting and to couple the driver and the dosing element during the dose dispensing.

9. The drug delivery device of claim 1, further comprising a spring configured to drive the dosing element during the dose dispensing.

10. The drug delivery device of claim 1, further comprising a display for indicating the selected dose, wherein the display comprises at least one belt having symbols for indicating the selected dose and being coupled to the dosing element such that rotation of the dosing element spools the belt.

11. The drug delivery device of claim 1, further comprising a dose limiter configured to inhibit the selected dose from exceeding an amount of liquid left in a cartridge of the drug delivery device.

12. The drug delivery device of claim 11, wherein the dose limiter comprises:
   a last dose nut coupled to the dosing element during the dose selecting such that rotation of the dosing element causes an axial movement of the last dose nut, and
   a stop element configured to block further movement of the last dose nut if the selected dose corresponds to the amount of liquid left in the cartridge.

13. The drug delivery device of claim 12, wherein the dose limiter further comprises a last dose sleeve rotationally coupled to the dosing element during dose selecting and rotationally de-coupled from the dosing element during dose dispensing, and wherein the last dose nut is coupled to the dosing element by the last dose sleeve.

14. The drug delivery device of claim 1, further comprising a nut with rotational hard stops wherein the dosing element comprises corresponding rotational stops interacting with the rotational hard stops of the nut for limiting axial movement of the nut.

15. The drug delivery device of claim 1, further comprising a cartridge containing the medicament.

16. A method of operating a drug delivery device, the method comprising:
    setting a dose of a medicament by rotating a dose selector rotationally coupled to a dosing element;
    pressing a button to dispense at least a portion of the dose of the medicament and to rotationally decouple the dose selector from the dosing element; and
    releasing the button such that the dosing element contacts the dose selector, whereby the dosing element rotates into a predefined rotational orientation with respect to the dose selector.

17. The method of claim 16, wherein releasing the button causes a spline of the dosing element to contact a spline of the dose selector such that the dosing element is guided to the predefined rotational orientation with respect to the dose selector.

18. The method of claim 17, wherein setting the dose of the medicament comprises rotating the dose selector when the spline of the dosing element is engaged with the spline of the dose selector such that rotation of the dose selector causes rotation of the dosing element.

19. The method of claim 16, wherein releasing the button causes the dosing element to rotate into the predefined rotational orientation with respect to the dose selector to rotationally couple the dosing element with the dose selector.

20. The method of claim 16, wherein pressing the button comprises releasing a spring to rotate the dosing element.

* * * * *